(12) United States Patent
Miller et al.

(10) Patent No.: US 10,589,054 B2
(45) Date of Patent: Mar. 17, 2020

(54) VALVE ASSEMBLIES

(71) Applicant: INTERSURGICAL AG, Vaduz (LI)

(72) Inventors: Andrew Neil Miller, Berkshire (GB); Matthew James Leary, Berkshire (GB)

(73) Assignee: Intersurgical AG, Vaduz (LI)

( * ) Notice: Subject to any disclaimer, the term of this patent is extended or adjusted under 35 U.S.C. 154(b) by 517 days.

(21) Appl. No.: 14/426,898

(22) PCT Filed: Sep. 6, 2013

(86) PCT No.: PCT/EP2013/068518
§ 371 (c)(1),
(2) Date: Mar. 9, 2015

(87) PCT Pub. No.: WO2014/037534
PCT Pub. Date: Mar. 13, 2014

(65) Prior Publication Data
US 2015/0231359 A1   Aug. 20, 2015

(30) Foreign Application Priority Data

Sep. 7, 2012 (GB) .................................... 1216006

(51) Int. Cl.
*A61M 16/20* (2006.01)
*A61M 16/08* (2006.01)
(Continued)

(52) U.S. Cl.
CPC ...... *A61M 16/208* (2013.01); *A61M 16/0057* (2013.01); *A61M 16/0825* (2014.02);
(Continued)

(58) Field of Classification Search
CPC .... A61M 16/00; A61M 16/127; A61M 16/20; A61M 16/208; A61M 16/209;
(Continued)

(56) References Cited

U.S. PATENT DOCUMENTS 3,417,795 A   11/1965  Hesse
3,688,794 A * 9/1972  Bird ...................... A61M 16/20
                                          128/205.24
(Continued)

FOREIGN PATENT DOCUMENTS

EP    0143618 A2   6/1985
EP    1512426 A1   3/2005
(Continued)

OTHER PUBLICATIONS

International Search Report and Written Opinion corresponding to PCT/EP2013/068518 dated Dec. 10, 2013.
(Continued)

*Primary Examiner* — Annette Dixon
(74) *Attorney, Agent, or Firm* — Pepper Hamilton LLP (57) ABSTRACT

A valve assembly comprising a fluid conduit (11,18) having an inlet and an outlet, and a valve seat (24) adapted to be engaged by a valve member (40) for controlling the flow of fluid through the outlet of the fluid conduit (11,18), wherein the valve assembly is defined by at least a valve body component (10) and a valve seat component (20) engaged therewith, the valve body component (10) defining at least part of the fluid conduit (11,18), and the valve seat component (10) defining at least the valve seat (24).

22 Claims, 4 Drawing Sheets (51) Int. Cl.
*A61M 16/00* (2006.01)
*F16K 15/14* (2006.01)

(52) U.S. Cl.
CPC ...... *A61M 16/0883* (2014.02); *A61M 16/201* (2014.02); *F16K 15/14* (2013.01); *A61M 16/205* (2014.02); *A61M 16/206* (2014.02); *A61M 2207/00* (2013.01); *Y10T 137/7879* (2015.04)

(58) Field of Classification Search
CPC .. B64D 17/30; B64D 25/06; B64D 2700/625; F16K 15/00; F17C 13/04; Y10T 137/785; Y10T 137/7905; Y10T 137/7932; A62B 9/02
USPC ............ 128/200.24, 204.18, 204.21, 205.24, 128/206.21, 207.12
See application file for complete search history.

(56) References Cited

U.S. PATENT DOCUMENTS

| | | | | |
|---|---|---|---|---|
| 3,726,274 A * | 4/1973 | Bird | ............ | A61M 16/00 128/205.24 |
| 3,933,171 A | 1/1976 | Hay | | |
| 4,190,045 A * | 2/1980 | Bartels | ............ | A61M 16/20 128/205.24 |
| 4,241,756 A * | 12/1980 | Bennett | ............ | A61M 16/20 137/496 |
| 4,454,893 A * | 6/1984 | Orchard | ............ | A61M 16/20 128/205.24 |
| 4,699,137 A * | 10/1987 | Schroeder | ............ | A61M 16/206 128/205.24 |
| RE32,553 E * | 12/1987 | Bennett | ............ | A61M 16/20 128/204.18 |
| 4,712,580 A * | 12/1987 | Gilman | ............ | A61M 16/20 128/204.18 |
| 4,898,165 A | 2/1990 | Warzeka | | |
| 5,020,532 A * | 6/1991 | Mahoney | ............ | A61M 16/20 128/204.18 |
| 5,063,925 A | 11/1991 | Frank et al. | | |
| 5,141,024 A | 8/1992 | Hicks | | |
| 5,360,000 A | 11/1994 | Carter | | |
| 6,073,630 A * | 6/2000 | Adahan | ............ | A61M 16/20 128/204.23 |
| 6,098,622 A | 8/2000 | Nobile et al. | | |
| 6,102,038 A * | 8/2000 | DeVries | ............ | A61M 16/208 128/204.23 |
| 6,217,555 B1 * | 4/2001 | Hart | ............ | A61B 17/3462 128/DIG. 26 |
| 6,230,708 B1 * | 5/2001 | Radko | ............ | A61M 16/00 128/200.24 |
| 6,609,515 B2 | 8/2003 | Bienvenu et al. | | |
| 2005/0098177 A1 * | 5/2005 | Haj-Yahya | ............ | A61M 16/208 128/204.18 |
| 2009/0250059 A1 * | 10/2009 | Allum | ............ | A61M 16/0051 128/204.26 |
| 2011/0126834 A1 | 6/2011 | Winter et al. | | |

FOREIGN PATENT DOCUMENTS

| | | |
|---|---|---|
| GB | 2303556 A | 2/1997 |
| GB | 2312038 A | 10/1997 |
| GB | 2404721 A | 2/2005 |
| GB | 2418973 A | 4/2006 |
| GB | 2487089 A | 7/2012 |
| WO | 00/45883 A1 | 8/2000 |

OTHER PUBLICATIONS

Great Britain Search Report corresponding to GB1216006.5 dated May 20, 2013.

* cited by examiner

VALVE ASSEMBLIES

This application is a national stage application under 35 U.S.C. § 371 of PCT Patent Application Serial No. PCT/EP2013/068518, filed Sep. 6, 2013, which claims the priority benefit of Great Britain Application No. 1216006.5, filed Sep. 7, 2012.

FIELD OF THE INVENTION

This invention relates to valve assemblies, and more particularly to valve assemblies for use with respiratory apparatus.

BACKGROUND OF THE INVENTION

When a patient is unable to breathe unaided, or requires assistance with breathing, the patient is usually connected to an artificial respiratory circuit including a ventilator programmed by a clinician to deliver an appropriate volume of air, or an air/oxygen mixture, to the patient. In such a respiratory circuit, it is desirable to prevent the patient from exhaling fully, and therefore the patient's lungs from deflating fully. This is because complete deflation, and subsequent reflation, of the patient's lungs requires a significant amount of the patient's energy.

Prevention of total exhalation is generally achieved by including a mechanism in the respiratory circuit which only allows exhaled breath above an appropriate exhalation pressure to escape the respiratory circuit through an exhalation port. Prevention of total exhalation in this way is known as applying "PEEP" to the respiratory circuit, where "PEEP" refers to Positive End Expiratory Pressure.

PEEP is currently applied to a respiratory circuit using either a so-called PEEP valve or an exhalation valve to control the passage of the exhaled breath through an exhalation port. A PEEP valve has a fixed and pre-determined release pressure for the exhalation port. An exhalation valve has a release pressure that is determined by the pressure of a gas within a control chamber of the exhalation valve. This gas within the control chamber is usually supplied by the ventilator at a pressure suitable to apply the desired positive end expiratory pressure to the respiratory circuit.

Conventionally, exhalation valves comprise a control chamber that is supplied by the ventilator, during use, with a gas under pressure, and a flexible membrane that defines a wall of the chamber and is disposed adjacent to a valve seat surrounding the exhalation port of the respiratory circuit. The flexible membrane is typically formed by a diaphragm or a balloon valve member.

In use, gas is supplied to the control chamber by the ventilator, and the supplied gas deforms the membrane elastically and outwardly from the chamber and into engagement with the valve seat, thereby sealing the exhalation port. The positive end expiratory pressure to be applied to the respiratory circuit is selected at the ventilator, and the ventilator supplies an appropriate pressure of gas to the control chamber to achieve that positive end expiratory pressure.

Different types of ventilator require there to be a different ratio between the pressure within the control chamber of the exhalation valve, and the airway pressure required to open the valve. This ratio is determined by the exhalation valve dimensions, including the diameter of the valve seat that surrounds the exhalation port, which means that different exhalation valves need to be used with different ventilators.

It is also necessary for the valve seat to be manufactured with a small tolerance in its diameter to achieve the desired accuracy in the pressure applied by the ventilator. However, the use of materials that are mouldable with small tolerances is expensive, and many such materials do not have the desired properties for other functions of the valve, eg low friction for use with a swivel connector.

The present invention overcomes or substantially mitigates some or all of the above mentioned and/or other disadvantages of the prior art.

SUMMARY OF THE INVENTION

According to a first aspect of the invention, there is provided a valve assembly comprising a fluid conduit having an inlet and an outlet, and a valve seat adapted to be engaged by a valve member for controlling the flow of fluid through the outlet of the fluid conduit, wherein the valve assembly is defined by at least a valve body component and a valve seat component engaged therewith, the valve body component defining at least part of the fluid conduit, and the valve seat component defining at least the valve seat.

According to a further aspect of the invention, there is provided a valve assembly kit comprising at least a valve body component and at least one valve seat component engageable therewith, the valve body component defining at least part of a fluid conduit having an inlet and an outlet, and the valve seat component defining at least a valve seat adapted to be engaged by a valve member for controlling the flow of fluid through the outlet of the fluid conduit.

The valve assembly kit according to the invention will typically further include the valve member for controlling the flow of fluid between the inlet and outlet of the fluid conduit.

The present invention is advantageous principally because the valve seat is formed in a different component to at least part of the fluid conduit. This enables the valve seat to be formed in a different material to the remainder of the valve assembly, such that materials that provide more accurate dimensions may be utilised for the valve seat, for example, without compromising the properties of the remainder of the valve assembly. Alternatively, or in addition, the present invention enables selection of a valve seat component from a range of components providing different valve seat configurations, thereby enabling assembly of a valve with the desired valve seat configuration.

The valve seat component and the valve body component may be distinct components in the valve assembly. The engagement between these components may be mechanical engagement only, with no bonding between the components by adhesive or otherwise. The valve body component and/or the valve seat component may be formed of plastics material. The valve body component and/or the valve seat component may be formed by injection moulding. The valve body component and the valve seat component may be injection moulded separately, such that there is no bonding of components during the injection moulding steps, eg the components are not multi-shot moulded, or co-moulded, together.

The valve body component may be configured to be engageable with any one of a range of different valve seat components, each having a different valve seat configuration. This enables the same valve body component to be included in valve assemblies having a range of different valve seat configurations. The valve body component and the valve seat component may be engaged during manufacture, eg before supply to the end user.

The present invention enables the construction of a valve assembly kit for supply to an end user, such that the end user may select the appropriate valve seat component for the intended use. The valve assembly kit may therefore be supplied with a plurality of valve seat components, each having a different configuration.

The valve assembly may be disposable. In this embodiment, the valve body component and the valve seat component are preferably permanently fixed together, following engagement. The valve body component and the valve seat component may be non-separable, without breaking one or both of the components. In alternative embodiments, the valve assembly may be reusable. The valve body component and the valve seat component may be separable, for example the valve seat component may be replaceable. This enables the valve assembly to be reused with different valve seat configurations between uses.

The fluid conduit of the valve assembly may comprise an inlet portion that extends from the inlet to the valve seat component, and an outlet portion that extends from the valve seat component to the outlet. The valve body component may define at least the inlet portion or the outlet portion of the fluid conduit. The valve body component may comprise a mount for the valve seat component. The valve seat component mount may be formed in a chamber of the valve assembly. The chamber may form part of the fluid conduit.

The chamber of the valve assembly may be defined by the valve body component together with the valve seat component and/or a separate closure component. The chamber may include an aperture to which the valve seat component is mounted, the valve seat either extending about the periphery of the aperture, or defining a further aperture in the fluid conduit.

The chamber may house the valve member. The valve member may form at least part of a partition in the chamber, such that a control chamber is defined that is sealed from the fluid conduit. The valve member may form a wall of the control chamber, such that the pressure of the gas(es) within the control chamber determine the threshold pressure of the gas(es) in the fluid conduit for movement of the valve member between open and closed configurations. Either the inlet portion or the outlet portion of the fluid conduit of the valve assembly may extend from the chamber. This portion of the fluid conduit may be formed in the valve body component. Alternatively, the outlet of the fluid conduit may be formed by one or more openings in a wall of the chamber. In addition, where a control chamber is included, a control line may extend from the control chamber. This control line may be formed in the valve seat component and/or a closure or partition component.

The valve seat component may be engageable with the valve body component by means of a mechanical attachment, for example a clip engagement. The engagement may be achieved using parts of the valve body component and the valve seat component only, such that no additional fasteners are required. The valve seat component may be adapted to engage the valve body component with either a close fit, or a snap fit, engagement. Alternatively, the valve seat component may include integral fasteners that are moveable into engagement with the valve body component.

The valve seat component may include one or more resiliently deformable engagement members, which are adapted to engage corresponding formations of the valve body component, eg with a snap fit. The engagement members may have the form of arms. In preferred embodiments, the engagement members are not disengageable from the valve body component, such that the valve seat component is not removable from the valve body component. However, in other embodiments, the engagement members are disengageable from the valve body component, such that the valve seat component is removable from the valve body component, for example by the valve assembly being configured to enable access to the engagement members by the end user. The engagement members of the valve seat component may define at least part of the fluid conduit, for example by defining at least part of the wall of the chamber in which the valve seat component is mounted.

The valve assembly may be configured such that at least part of the valve seat component is visible during use. The valve seat component may therefore include an indicator that is visible to the end user, and may provide information regarding the valve seat configuration. This indicator may be the colour of the visible part of the valve seat component, or may be indicia on a visible surface of the valve seat component. The valve seat component may be configured to define a wall of the valve assembly, such as a wall of the chamber of the valve assembly, such that part of the valve seat component is visible during use.

The valve seat component may include a handle or grip for facilitating engagement with the valve body component. The valve seat component may include an indication of the correct orientation for assembly, and may be adapted to prevent engagement in an incorrect orientation. In one embodiment, a handle of the valve seat component prevents engagement with the valve body component in an incorrect orientation The valve body component may cooperate with the valve seat component and the valve member only to form a functioning valve assembly, or there may be at least one additional closure component. However, the valve member may have the form of an assembly that includes provision of a control chamber and control line. The valve body component may define both the inlet and outlet of the fluid conduit. Alternatively, the valve body component may define either the inlet or the outlet, with the other being defined by another component, for example either the valve seat component or a closure component. The valve body component may be more substantial than the valve seat component, and may constitute the majority of the valve assembly (by weight).

The valve seat component may define, in addition to a valve seat, at least part of the fluid conduit. The valve seat component may be adapted for in-line connection with a valve body component, such that these components respectively define portions of the fluid conduit upstream and downstream of the valve seat. Alternatively, the valve seat component is engageable with a mount of the valve body component, such that the valve body component defines, at least partially, portions of the fluid conduit upstream and downstream of the valve seat. Where the valve body component includes a mount for the valve seat component within a chamber, the valve seat component may form the closure for the chamber, or a separate closure component may be provided.

The valve member may be movable or deformable relative to the valve seat component to control the flow of fluid between the inlet and outlet of the fluid conduit. The valve member may be engageable with the valve seat to partially close, or entirely close, the fluid conduit at the valve seat. The valve member may therefore be moveable between an open configuration in which flow of fluid is permitted between the inlet and outlet of the fluid conduit, and a closed configuration in which flow of fluid is either prevented between the inlet and outlet of the fluid conduit, or restricted between the inlet and outlet of the fluid conduit relative to the open configuration. The valve member may be a flexible membrane disposed adjacent to the valve seat. The flexible membrane is typically formed by a diaphragm or a balloon valve member, which may be deformed into engagement with the valve seat. The valve member may be a separate component from the valve body component.

The present invention enables the valve seat to be formed in a different material to the remainder of the valve assembly, such that materials that provide more accurate dimensions may be utilised for the valve seat, for example, without compromising the properties of the remainder of the valve assembly. It is believed that this feature is inventive, even where the valve body and the valve seat are formed together.

Hence, according to a further aspect of the invention, there is provided a valve assembly or a valve assembly kit comprising a fluid conduit having an inlet and an outlet, and a valve seat adapted to be engaged by a valve member for controlling the flow of fluid through the outlet of the fluid conduit, wherein the valve seat is formed of a different material to at least part of the fluid conduit.

The valve seat may be formed in a material that is mouldable with dimensions that are within very low tolerances, for example such that the tolerance of the width or diameter of the valve seat is preferably less than +/−0.5 mm, and more preferably +/−0.4 mm or less. The component may be formed from an engineering polymer. The engineering polymer may be acrylonitrile butadiene styrene (ABS). The fluid conduit may be formed of a plastics material with different properties, such as High Density Polyethylene (HDPE), and indeed the majority of the valve assembly, save for the valve seat, may be formed in such a material.

The present inventions are particularly advantageous in the field of valve assemblies for use in respiratory circuits. In particular, the valve assembly according to the invention may be an exhalation valve assembly, which may control the flow of exhalation gases through an exhalation port either to atmosphere in an open circuit, or to the ventilator in a closed circuit.

According to a further aspect of the invention, there is provided a respiratory circuit comprising a valve assembly as described above. The valve assembly may be an exhalation valve assembly.

The respiratory circuit may comprise a ventilator, an inhalation limb for supplying inhalation gases to the patient, an exhalation limb for conveying exhalation gases away from the patient, and a valve assembly according to the invention. The inhalation limb and exhalation limb may be defined by the same passageway, or may be formed by separate passageways. A patient interface device may be provided. The patient interface device may be a non-invasive device, such as a mouthpiece or a respiratory mask. Alternatively, the patient interface device may be an invasive device, such as an endotracheal tube. The valve assembly may be an exhalation valve assembly that controls flow of exhalation gases through an exhalation port, eg in the exhalation limb.

The exhalation valve assembly may be adapted to apply a Positive end expiratory pressure (PEEP) to the respiratory circuit. The exhalation valve may have a fixed and predetermined release pressure for the exhalation port. Alternatively, the exhalation valve may have a release pressure that is determined by the pressure of a gas within a control chamber of the exhalation valve. This gas within the control chamber may be supplied by the ventilator at a pressure suitable to apply the desired positive end expiratory pressure to the respiratory circuit.

The exhalation valve assembly may comprise a control chamber that is supplied by the ventilator, during use, with a gas under pressure, and a flexible membrane that defines a wall of the chamber and is disposed adjacent to the valve seat, which may surround the exhalation port of the respiratory circuit. The flexible membrane may be formed by a diaphragm or a balloon valve member.

In use, gas may be supplied to the control chamber by the ventilator, and the supplied gas may deform the membrane elastically and outwardly from the control chamber and into engagement with the valve seat, thereby sealing the exhalation port. The positive end expiratory pressure to be applied to the respiratory circuit is selected at the ventilator, and the ventilator supplies an appropriate pressure of gas to the control chamber to achieve that positive end expiratory pressure.

The valve seat components that are supplied as part of the valve assembly kit according to the present invention may have valve seat diameters that correspond to the operating requirements of different ventilators, or alternatively different settings or modes of the same ventilator.

According to a further aspect of the invention, there is provided a method of manufacturing a valve assembly comprising the steps of:
(a) providing a valve body component defining at least part of a fluid conduit of the valve assembly having an inlet and an outlet;
(b) providing at least one valve seat component defining at least a valve seat adapted to be engaged by a valve member for controlling the flow of fluid through the outlet of the fluid conduit of the valve assembly; and
(c) engaging the at least one valve seat component with the valve body component.

The valve seat component and the valve body component may be distinct components. The engagement between these components may be mechanical engagement only, with no bonding between the components by adhesive or otherwise. The valve body component and/or the valve seat component may be formed of plastics material. The valve body component and/or the valve seat component may be formed by injection moulding. The valve body component and the valve seat component may be injection moulded separately, such that there is no bonding of components during the injection moulding steps, eg the components are not multi-shot moulded, or co-moulded, together.

BRIEF DESCRIPTION OF THE FIGURES

An embodiment of the invention will now be described in detail, for illustration only, with reference to the accompanying figures, in which.

DETAILED DESCRIPTION OF THE INVENTION

Figure 1:
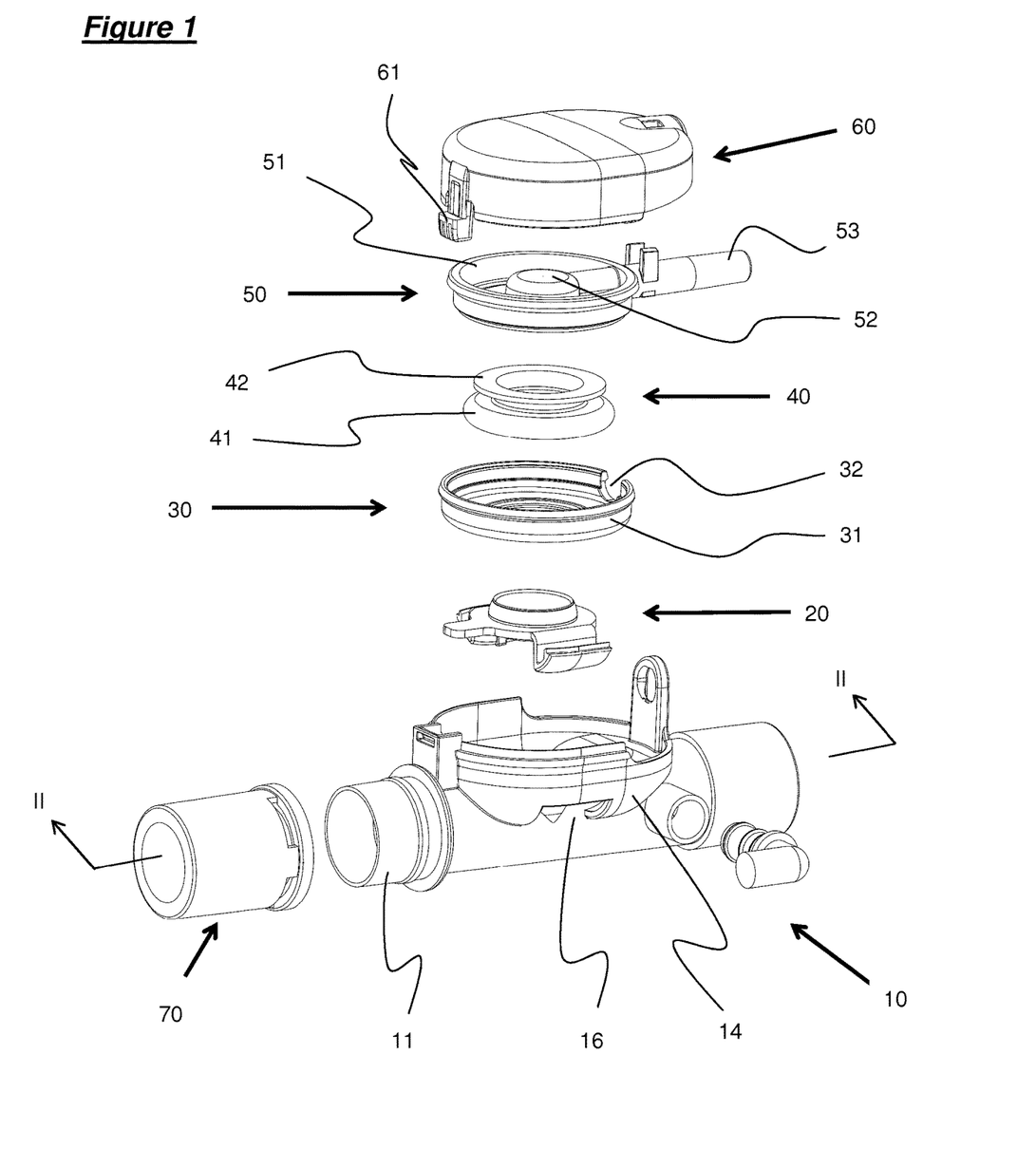
FIG. 1 is an exploded view of a valve assembly according to the invention.
Figure 2:
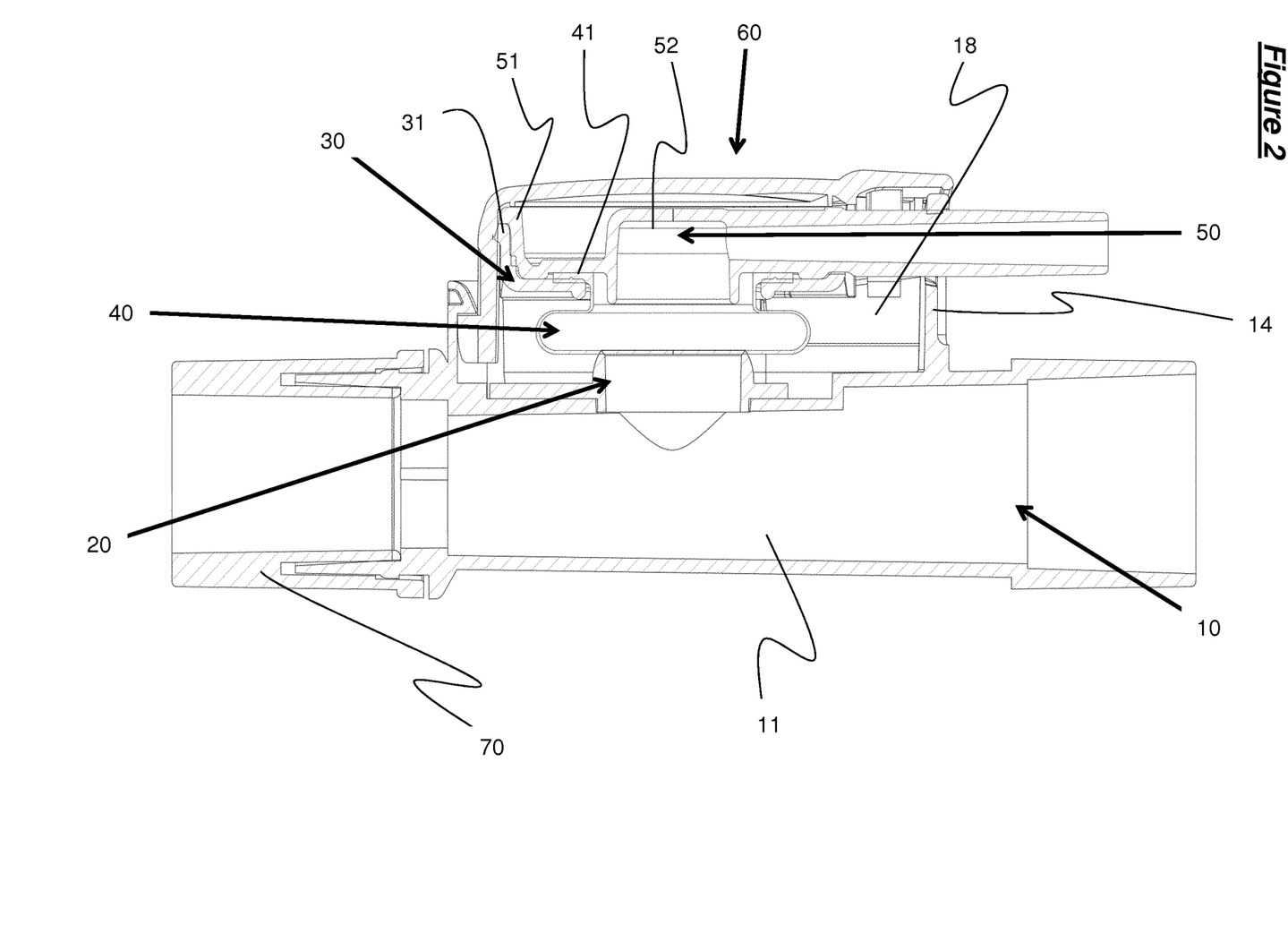
FIG. 2 is a cross-sectional view of the valve assembly of FIG. 1, along the line II-II in FIG. 1.

A valve assembly according to the invention is shown in FIGS. 1 and 2, and comprises a valve body component 10, a valve seat component 20, a support ring 30, a balloon valve member 40, a chamber component 50, a cap 60, a swivel connector 70 and a swivel elbow 80.

Figure 3:
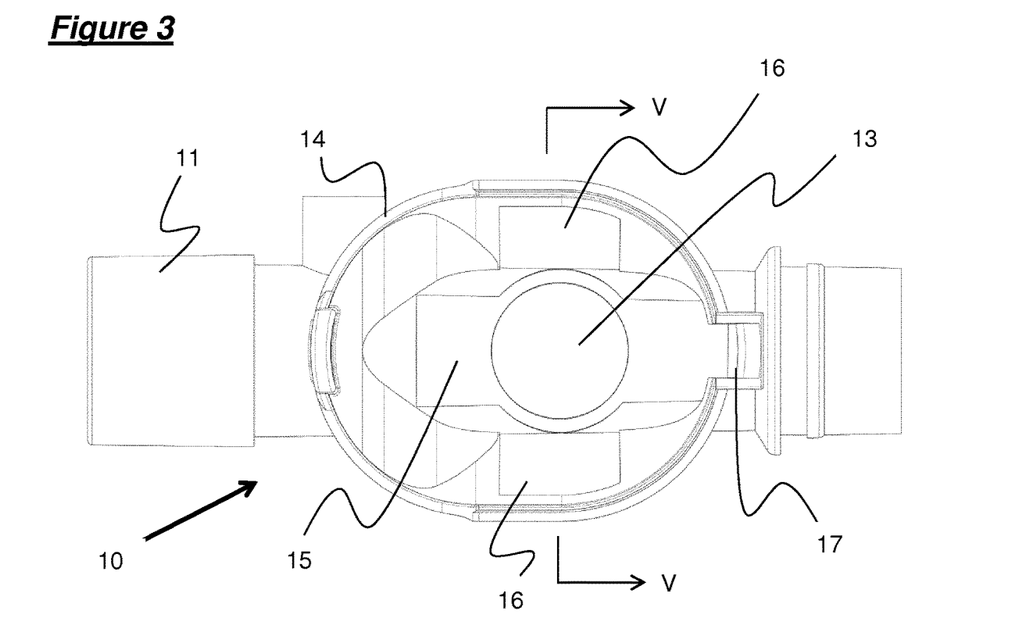
FIG. 3 is a plan view of a valve body component that forms part of the valve assembly of FIGS. 1 and 2.

The valve body component 10, which is also shown in isolation in FIG. 3, comprises a breathing tube 11, an exhalation port 13 located in an upper wall of the breathing tube 11, and a valve housing 14. A shallow rectangular recess is provided on the upper surface of the breathing tube 11 so as to define a flat platform 15, which lies in the horizontal plane, and within which an aperture that defines the exhalation port 13 is formed. The valve housing 14 is provided on the upper surface of the breathing tube 11. The valve housing 14 encompasses the exhalation port 13, and is upwardly open. The valve housing 14 is generally bathtub-shaped in that the side walls of the valve housing 14 connect to the wall of the breathing tube 11 and curve in a plane that is perpendicular to the axis of the breathing tube 11, with free ends that extend generally vertically upwards. The long axis of the valve housing 14 extends in a direction parallel to the axis of the breathing tube 11.

The longer sides of the valve housing 14 are each provided with a generally rectangular cut-out 16 in a portion of the side wall that is adjacent to the wall of the breathing tube 11. The presence of the cut-outs 16 means that a portion of each of the longer sides of the valve housing 14 has a free lower end. One end of the valve housing 14 is also provided with an upwardly open fastener socket 17 having a rectangular cross-section.

Figure 4:
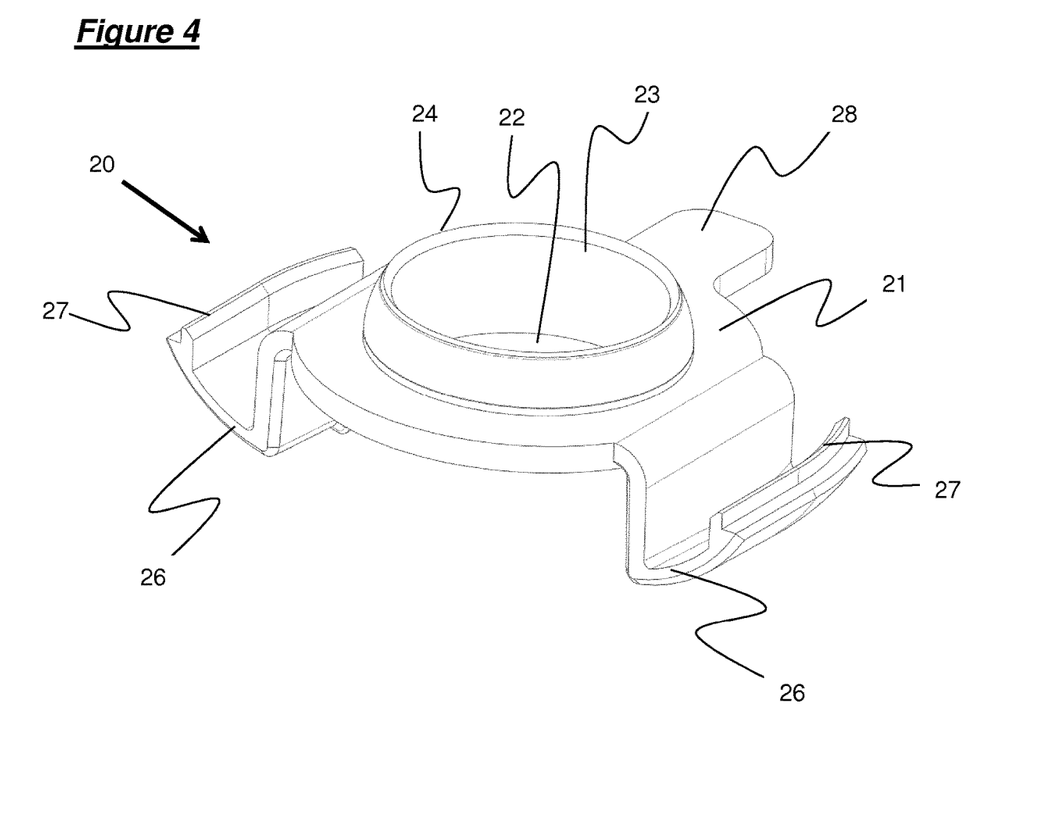
FIG. 4 is a perspective view of a valve seat component that forms part of the valve assembly of FIGS. 1 and 2.

The valve seat component 20, which is shown in isolation in FIG. 4, comprises a generally circular base plate 21 having a central circular opening 22, the opening 22 being concentric with the base plate 21. An upstanding collar 23 is provided on the upper surface of the base plate 21, at the periphery of the opening 22. The inwardly facing surface of the collar 23 is cylindrical, whereas the outer surface of the collar 23 is curved, such that the collar 23 is thicker at its lower end than its upper end. The upper surface of the collar 23 is radially inwardly bevelled to form an uppermost edge that defines a valve seat 24.

The valve seat component 20 also comprises a pair of retaining arms 26 that extend from diametrically opposed positions at the periphery of the base plate 21.

Each retaining arm 26 comprises a generally rectangular planar portion that depends downwardly from the base plate 21. The rectangular planar portion is generally flat and lies in the vertical plane. The rectangular planar portion connects to the base plate by a rounded shoulder. The retaining arm is also provided with a curved portion having the same width as the rectangular planar portion, and extending generally diagonally upwardly from the lower edge of that portion, following a slightly curved path. The curvature is in a plane perpendicular to the plane of the base plate 21. A portion of the curved portion is also curved in the plane of the base plate 21, and has the same sense of curvature as the base plate 21, such that the curved portion of each retaining arm 26 corresponds dimensionally to the valve housing 14. The curved portion terminates in a plane that is slightly below the plane in which the base plate 21 lies.

A locating wall 27 is provided that extends upwardly from the inner surface of the curved portion of each retaining arm 26, at a location close to the free end of the curved portion. The locating wall 27 defines a generally flat, outwardly-facing surface and a generally flat, inwardly-facing surface. The upper edge of the wall is bevelled so as to face radially inwardly and upwardly. The free edge of the curved portion of each retaining arm 26 is provided with a generally flat, upwardly-facing surface which is located adjacent to the locating wall 27, such that together the two surfaces define an outwardly and upwardly open, V-shaped locating channel.

An orientating tab 28 is provided at the periphery of the base plate 21, at an angular position that is mid-way between the two retaining arms 26. The tab 28 is generally rectangular in shape, having the same thickness and lying in the same plane as the base plate 21. The two corners at the free end of the tab 28 are curved in the plane of the base plate 21.

The valve seat component 20 is formed in an engineering polymer, typically ABS (acrylonitrile butadiene styrene), by single-shot injection moulding.

Figure 5:
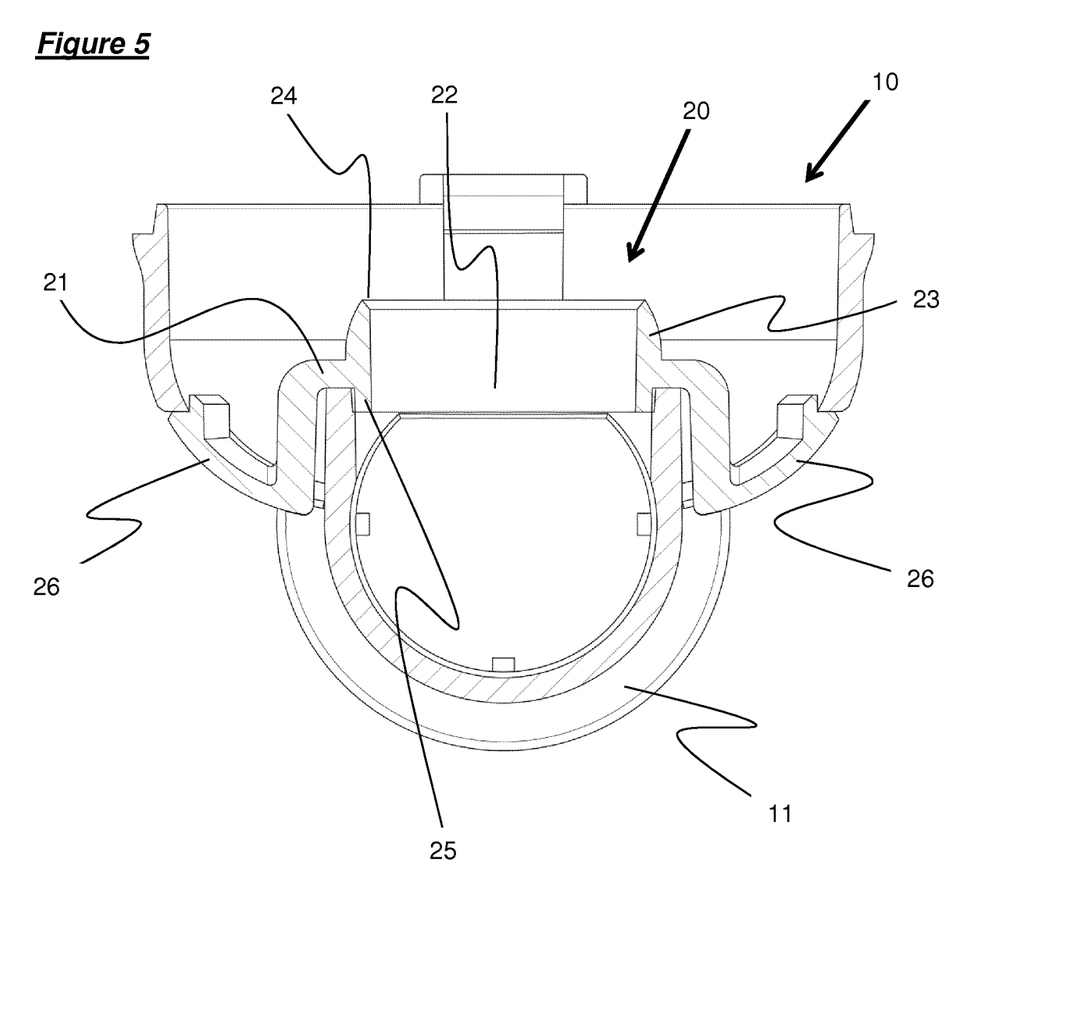
FIG. 5 is a cross-sectional view of the valve body component, along the line V-V in FIG. 3, with the valve seat component engaged therewith.

During assembly, the valve seat component 20 is brought into contact with the valve body component 10, such that the skirt 25 of the valve seat component 20 is received with a close fit within the exhalation port 13. The retaining arms 26 are inserted into the cut-outs 16 in the valve housing 14. The resilience of the retaining arms 26 allows the retaining arms 26 to bend inwardly slightly on insertion so that the outer surface of the curved portion of each retaining arm 26 is able to move beyond the lower free end of the long side wall of the valve housing 14. This causes the inner edges of the lower free ends of the valve housing 14 to be received in the V-shaped locating channels of the valve seat component 20, thereby preventing the valve seat component 20 from being able to move upwardly, and hence fixing the valve seat component 20 to the valve body component 10.

The orientating tab 28 of the valve seat component 20 is received on the platform 15 of the valve body component 10 that is dimensioned to accommodate it, i.e., adjacent to the fastener socket 17. This is to ensure that the user has orientated the valve seat component 20 correctly.

The balloon valve member 40 comprises a disc-shaped enclosure 41, with concave side walls, and a central, circular entrance in an upper wall of the balloon valve member 40. A connecting formation 42 is also provided, which comprises an 25 upstanding skirt that extends from the entrance to the enclosure 41, and an annular connecting flange that projects outwardly therefrom.

The support ring 30 has an annular engagement formation 31, which comprises a planar annular portion, and an upstanding skirt at the periphery of the annular portion. The annular portion of the annular engagement formation 31 fits about the upstanding skirt of the connecting formation 42 of the balloon valve member 40, between the disc-shaped enclosure 41 and the annular connecting flange of the connecting formation 42, when assembled. The upstanding skirt of the support ring 30 also includes an upwardly open recess 32 that accommodates the control line of the chamber component 50, as discussed below.

The chamber component 50 comprises an annular engagement formation 51, which comprises a planar annular portion, and a skirt that extends upwardly from the periphery of the planar annular portion. The annular engagement formation 51 of the chamber component 50 is received, with a close fit, within the annular engagement formation 31 of the support ring 30, such that corresponding fastening formations on the upstanding skirts of the engagement formations 31,51 fix the components 30,50 together.

The annular connecting flange of the connecting formation 42 of the balloon valve member 40 is captivated between the engagement formations 31,51 of the support ring 30 and the chamber component 50, with the engagement formation 51 of the chamber component 50 having an annular recess in its lower surface to accommodate the connecting formation 42 of the balloon valve member 40. This arrangement provides hermetically sealed, fluid communication between the disc-shaped enclosure 41 of the balloon valve member 40, and a chamber portion 52 of the chamber component 50.

The chamber portion 52 of the chamber component 50 is cylindrical in shape, with a closed upper end, and an open lower end in fluid communication with the disc-shaped enclosure 41 of the balloon valve member 40. A tubular control line 53 extends radially outwardly from a side wall of the chamber portion 52, and extends through the upstanding skirt of the engagement formation 51 of the chamber component 50, as well as through the recess 32 in the support ring 30 when assembled.

The outer end of the control line 53 is adapted for connection to a supply of gas, and is in fluid communication with the chamber portion 52 of the chamber component 50. When gas is supplied to the control line 53, before use, the disc-shaped enclosure 41 of the balloon valve member 40 will inflate into engagement with the valve seat 24 of the valve seat component 20.

The valve housing 14 of the valve body component 10 is substantially closed by the cap 60, which includes a fastening lug 61 that engages the fastener socket 17 of the valve body housing with a snap fit. The cap 60 substantially closes the valve housing 14, thereby defining an exhalation chamber 18, which surrounds the exhalation port 13. However, a pair of exhalation slots are defined between the cap 60 and the upper edge of the valve housing 14, from which exhalation gases may escape from the exhalation chamber 18 to the atmosphere.

The valve body component 10 also includes a sampling port, including a swivel elbow 80, and one end of the breathing tube 11 includes a swivel connector 70 for connection to an exhalation limb of a respiratory circuit. The other end of the breathing tube 11 is adapted for connection to the ventilator, as is the control line 53.

In use, when the gas pressure in the breathing tube 11 exceeds a threshold pressure, the upward pressure caused by that gas on the lower surface of the balloon valve member 40 causes the balloon valve member 40 to deform so as to displace a portion of the balloon valve member 40 out of contact with the valve seat 24, thus creating a passageway defined between the valve seat 24 and the lower surface of the balloon valve member 40, which extends from the exhalation port 13 to the exhalation chamber 18. Exhalation gases pass through this passageway, into the exhalation chamber 18, and then through the exhalation slots to the atmosphere, in use.

The pressure of the gas within the disc-shaped enclosure 41 is determined by a ventilator, such that the threshold pressure required within the breathing tube 11 of the valve body component 10 to disengage the balloon valve member 40 from the valve seat 24, and hence allow passage of exhalation gases through the exhalation port 13, i.e. the Positive End Expiratory Pressure (the PEEP), is at a predetermined value.

The ratio between the pressure of gas supplied through the control line 53 and the threshold exhalation pressure required to open the valve, ie the PEEP, is determined by the dimensions of the valve assembly, including the diameter of the valve seat 24. The valve assembly according to the present invention therefore enables valve seat components 20 having different valve seat diameters to be engaged with the valve body component 10, such that the valve assembly functions with different ventilators, for example. In addition, the valve seat component may be formed of a precision engineering polymer, such that the valve diameter is known to within a small degree of error.

The invention claimed is:

1. An exhalation valve assembly comprising a fluid conduit having an inlet and an outlet, an exhalation port, a control chamber adapted to be supplied by a ventilator, during use, with a gas under pressure, a flexible membrane that defines a wall of the control chamber, and a valve seat component defined by an upstanding collar at the periphery of an opening into the exhalation port, the flexible membrane being disposed adjacent to an uppermost edge of the upstanding collar, such that the uppermost edge of the upstanding collar is adapted to be engaged by the flexible membrane, during use, and the exhalation valve assembly has a release pressure that is determined by the pressure of one or more gases within the control chamber, wherein the exhalation valve assembly is defined by at least a valve body component and the valve seat component, which is engageable therewith, the fluid conduit of the exhalation valve assembly comprising an inlet portion that extends from the inlet of the fluid conduit to the valve seat component, and an outlet portion that extends from the valve seat component to the outlet of the fluid conduit, the valve seat component defining at least part of the inlet portion of the fluid conduit, and the valve seat component comprising, and defining a configuration of, at least the uppermost edge of the upstanding collar.

2. The exhalation valve assembly as claimed in claim 1, wherein the valve body component and the valve seat component are permanently fixed together, following engagement.

3. The exhalation valve assembly as claimed in claim 1, wherein the valve body component comprises a mount for the valve seat component, the mount being formed in a chamber of the valve assembly that forms part of the fluid conduit.

4. The exhalation valve assembly as claimed in claim 3, wherein the chamber houses the flexible membrane, and the flexible membrane forms at least part of a partition in the chamber, such that a control chamber is defined that is sealed from the fluid conduit.

5. The exhalation valve assembly as claimed in claim 1, wherein the valve assembly comprises a mechanical attachment for engagement of the valve seat component with the valve body component.

6. The exhalation valve assembly as claimed in claim 1, wherein the valve seat component includes one or more resiliently deformable engagement members, which are adapted to engage corresponding formations of the valve body component.

7. The exhalation valve assembly as claimed in claim 1, wherein the valve assembly is configured such that at least part of the valve seat component is visible during use.

8. The exhalation valve assembly as claimed in claim 7, wherein the valve seat component includes an indicator that is visible to the end user, which provides information regarding the valve seat configuration.

9. The exhalation valve assembly as claimed in claim 7, wherein the valve seat component is configured to define a wall of the valve assembly, such that part of the valve seat component is visible during use.

10. The exhalation valve assembly as claimed in claim 1, wherein the uppermost edge of the upstanding collar is formed of a different material to at least part of the fluid conduit.

11. An exhalation respiratory circuit comprising an exhalation valve assembly as claimed in claim 1.

12. The exhalation respiratory circuit as claimed in claim 11, wherein the respiratory circuit further comprises a ventilator, an inhalation limb for supplying inhalation gases to the patient, an exhalation limb for conveying exhalation gases away from the patient.

13. The exhalation respiratory circuit as claimed in claim 11, wherein the exhalation valve assembly controls flow of exhalation gases through an exhalation port.

14. The exhalation valve assembly as claimed in claim 1, wherein the valve body component and the valve seat component are formed as separate components and engaged together prior to use.

15. A method of manufacturing an exhalation valve assembly comprising the steps of:
  (a) providing a valve body component defining at least an inlet portion of a fluid conduit of the valve assembly having an inlet and an outlet;
  (b) providing at least one valve seat component defined by an upstanding collar at the periphery of an opening into an exhalation port comprising, and defining a configuration of, at least an uppermost edge of the upstanding collar adapted to be engaged by a flexible membrane for controlling the flow of fluid through the outlet of the fluid conduit of the valve assembly; and
  (c) engaging the at least one valve seat component with the valve body component, such that the inlet portion of the fluid conduit extends from the inlet of the fluid conduit to the valve seat component, and the fluid conduit comprises an outlet portion that extends from the valve seat component to the outlet of the fluid conduit,
  wherein the valve assembly has a control chamber adapted to be supplied by a ventilator, during use, with a gas under pressure, and the flexible membrane defines a wall of the control chamber and is disposed adjacent to the uppermost edge of the upstanding collar, such that the exhalation valve assembly has a release pressure for the outlet that is determined by the pressure of one or more gases within the control chamber.

16. The method of manufacturing an exhalation valve assembly as claimed in claim 15, wherein the engagement between the valve seat component and the valve body component is mechanical engagement only, with no bonding between the components by adhesive or otherwise.

17. The method of manufacturing an exhalation valve assembly as claimed in claim 15, wherein the valve body component and/or the valve seat component are formed by injection moulding.

18. The method of manufacturing an exhalation valve assembly as claimed in claim 17, wherein the valve body component and the valve seat component are injection moulded separately, such that there is no bonding of components during the injection moulding steps and the components are not multi-shot moulded, or co-moulded, together.

19. An exhalation valve assembly comprising a fluid conduit having an inlet and an outlet, an exhalation port, a control chamber adapted to be supplied by a ventilator, during use, with a gas under pressure, a flexible membrane that defines a wall of the control chamber and a valve seat component defined by an upstanding collar at the periphery of an opening into the exhalation port, the flexible membrane being disposed adjacent to an uppermost edge of the upstanding collar, the flexible membrane having an engaged position with respect to the uppermost edge of the upstanding collar to provide a closed configuration of the exhalation valve assembly and a partially disengaged position with respect to the valve seat to provide an open configuration of the exhalation valve assembly, and the exhalation valve assembly has a release pressure that is determined by the pressure of one or more gases within the control chamber, wherein the exhalation valve assembly is defined by at least a valve body component and a valve seat component engageable therewith, the fluid conduit of the exhalation valve assembly comprising an inlet portion that extends from the inlet of the fluid conduit to the valve seat component, and an outlet portion that extends from the valve seat component to the outlet of the fluid conduit, the valve body component defining at least part of the inlet portion of the fluid conduit, and the valve seat component comprising, and defining a configuration of, at least the uppermost edge of the upstanding collar.

20. The exhalation valve assembly as claimed in claim 19, wherein the flexible membrane is moveable or deformable relative to the uppermost edge of the upstanding collar to control the flow of fluid between the inlet and outlet of the fluid conduit.

21. The exhalation valve assembly as claimed in claim 19, wherein the flexible membrane is movable or deformable relative to the uppermost edge of the upstanding collar to control the flow of fluid through a space between the flexible membrane and the uppermost edge of the upstanding collar, thereby controlling the flow of fluid between the inlet and outlet of the fluid conduit.

22. The exhalation valve assembly as claimed in claim 19, wherein the flexible membrane is movable or deformable between the open configuration, in which there is a space between the flexible membrane and the uppermost edge of the upstanding collar, and the closed configuration, to control the flow of fluid through the space between the flexible membrane and the uppermost edge of the upstanding collar and thereby control the flow of fluid between the inlet and outlet of the fluid conduit.

* * * * *